(12) United States Patent
Kirollos et al.

(10) Patent No.: US 6,284,198 B1
(45) Date of Patent: Sep. 4, 2001

(54) SELF APPEARING WARNING SIGN DEVICE AND METHOD OF MANUFACTURE

(75) Inventors: Kirollos Salama Kirollos; Gueorgui Milev Mihaylov, both of Virginia Beach, VA (US)

(73) Assignee: K&M Environmental Inc., Virginia Beach, VA (US)

( * ) Notice: Subject to any disclaimer, the term of this patent is extended or adjusted under 35 U.S.C. 154(b) by 0 days.

(21) Appl. No.: 09/163,528

(22) Filed: Sep. 30, 1998

(51) Int. Cl.[7] .............................. G01J 1/50; G01N 31/22; G01N 21/00
(52) U.S. Cl. .................. 422/87; 422/58; 422/86; 422/56; 422/57; 436/164; 436/170
(58) Field of Search .................. 422/58, 86, 87, 422/119, 902, 57, 60; 436/170, 164

(56) References Cited

U.S. PATENT DOCUMENTS

| | | | |
|---|---|---|---|
| 3,681,027 | * 8/1972 | Smith | 422/55 |
| 4,205,043 | * 5/1980 | Esch et al. | 422/56 |
| 4,421,719 | * 12/1983 | Burleigh | 422/57 |
| 4,472,353 | * 9/1984 | Moore | 422/58 |
| 4,478,792 | * 10/1984 | McConnaughey et al. | 422/56 |
| 4,495,291 | * 1/1985 | Lawton | 436/1 |
| 4,772,560 | * 9/1988 | Attar | 436/165 |
| 4,783,316 | * 11/1988 | Pannwitz | 422/58 |
| 5,192,500 | * 3/1993 | Treddenick | 422/56 |
| 5,364,593 | * 11/1994 | Mihaylov et al. | 422/87 |
| 5,411,709 | * 5/1995 | Furuki et al. | 422/91 |
| 5,650,329 | * 7/1997 | Warner | 436/101 |

* cited by examiner

Primary Examiner—Jill Warden
Assistant Examiner—LaToya Cross

(57) ABSTRACT

A self-appearing warning sign device and method for the manufacture of a self-appearing warning sign device including a relatively thin gas impermeable support member upon which a coating is superimposed having a composition containing one or more chromographic reagents which will cause a visible color change in the presence of a specified polluting gas. The coating has a raised thickness of between about 5–500 microns. A warning sign of defined shape is formed depositing the coating composition in a given shape identifying the presence of the polluting gas or by masking a given area to form said shape. The device also includes a hydrophobic layer and end covers in an arrangement forming a gas tight sealed enclosure except for an opening in each cover on opposite ends of the device.

10 Claims, 9 Drawing Sheets

SECTION "A-A"

SECTION "A-A"

SECTION "A-A"

a) DANGER
b) POISON
c) WARNING
d) HAZARD
e) HF
f) H$_2$S g)    h)    i)    j)

SELF APPEARING WARNING SIGN DEVICE AND METHOD OF MANUFACTURE

FIELD OF THE INVENTION

This invention relates to a self-appearing warning sign device and a method for the manufacture of a self-appearing warning sign device which will function as a colorimetric dosimeter for visual or electronic detection or which will function as a warning label or tag as to the presence of a specific polluting toxic gas/vapor in the ambient environment.

BACKGROUND OF THE INVENTION

Numerous warning signs and labels exist to warn of the presence of hazards in the surrounding environment. All of these warning signs and labels are displayed by a user with prior knowledge of the existence of the hazard so as to warn and alert others. For example, a warning sign having a flame shape or the word "FLAMMABLE" can be displayed by the user next to flammable substances to warn others of the existence of these substances.

Colorimetric dosimeter devices have been developed for measuring the concentration levels of gaseous hazards or pollutants in the ambient atmosphere surrounding the dosimeter. Colorimetric dosimeters are also available commercially as portable devices or badges. The conventional dosimeter badge contains a color-forming reagent impregnated in paper, which reacts by changing color in the presence of a particular gastapor. The intensity of the color change is proportional to the concentration of the reactive gas/vapor and the time of exposure. This relationship allows the observer to compare the received color to a standard color to determine the real exposure. However, the conventional dosimeter badge does not, by itself, function as a warning sign or a warning label.

In the present invention, the user has knowledge of the potential existence of the hazard but the warning sign appears only when the targeted hazard starts to exist even in very small quantities, not dangerous to health, allowing the user to take corrective measures As the amount of the targeted hazard increases in the surrounding environment, the color and intensity of the warning sign increases in a direct proportional manner to the concentration of the hazard. This feature gives the self-appearing warning sign dosimetric properties enabling the user to estimate or accurately measure, in real time, the amount of hazard in the surrounding environment. The self-appearing warning sign of the present invention is a base for light-weight and low-cost colorimetric dosimeters suitable as disposable devices or warning labels. The device made upon the present invention is scratchproof and virtually waterproof suitable for harsh indoor and outdoor industrial environments.

SUMMARY OF THE INVENTION

It is a general objective of the present invention to overcome the drawbacks of the prior art by providing a self-appearing warning sign, method and arrangements for manufacturing in such a way that the visualization of the hazard will allow immediate, on-site, real-time visual warning of the presence of the hazard(s).

Another objective of the present invention is to provide the said method and arrangement in such a way that the visualization of the hazard will allow on-site, immediate, real-time measurements by visual observation or electronic means.

Still another objective of the present invention is to provide a fast-acting and universally usable method and arrangements warning for the presence and measuring the concentration of highly toxic substances at parts per billion levels.

Yet another objective of the present invention is to provide a method and arrangements for visually warning of the presence and measuring the concentration of the targeted toxic substance in a simple manner clearly visible and understandable to the layman.

A further objective of the present invention is to provide a method for manufacturing and arrangements for the self-appearing warning sign to allow warning the presence of, and measuring the concentration of the targeted toxic substance at low cost, and therefore enabling thousands of workers at industrial plants to use it on a daily basis without significant financial or economical consequences.

Another objective of the present invention is to provide a method and arrangements for warning of the presence and measuring the concentration of the targeted toxic substances under extreme environmental and harsh industrial conditions.

In accordance with these objectives and others which will become apparent hereinafter, a general feature of the present invention resides and is briefly stated as a self-appearing warning sign and a method and arrangements for manufacturing of the device which will visually warn and calorimetrically measure the presence and the concentration of certain toxic gases and vapors in the surrounding environments. More particularly, the invention relates to a self-appearing warning sign, label or parts of warning signs and labels. The warning sign appears when a certain level of a possible contaminant exceeds a preset, predetermined and pre-adjusted value. The invention utilizes a flat indicating layer, applied on inert, transparent or opaque flat surfaces. The said flat indicating layer, composed of a chemical or a mixture of chemical ingredients is capable of changing color in a reversible or irreversible manner in the presence of the targeted hazard or contaminant. In the present invention only part of the said indicating layer is in contact with the surrounding atmosphere. This part is shaped and configured to resemble well known warning symbols, for example: an exclamation point inside a triangle, a flame shape, "ACID", "CORROSIVE", "COMBUSTIBLE", "PEROXIDE", "DANGER", "FLAMMABLE", "PHOSGENE", "HYDRAZINE", "TDI", etc. As a result of said reaction the said part forms a warning sign by the color contrast between the configured part of the layer and the background.

In accordance with these features, the said indicating layer is covered with a screen(s) permeable or semi-permeable to light, gas and vapor diffusion. The said screen(s) is constructed in a manner to allow visual observance and/or electronic measurement of the color developed on the said indicating layer, yet not allowing liquid droplets and solid particles from contacting the said indicating layer. Another function of the said screen is to act as a windbreaker, considerably reducing the effect of the surrounding air velocity on the measurement process.

Another feature of the invention is that all of the various parts of the arrangements are mounted in a small and light weight housing which can be worn near the breathing zone of a person without disturbing or affecting his or her job activities.

Yet another feature of the invention is that all of the various members of the arrangements of the said warning sign are constructed from low-cost materials suitable for disposable applications, thereby allowing for more frequent use, hence promoting high-standards of safety and industrial hygiene practices.

For the warning sign to be visibly responsive to the presence of a targeted toxic gaseous substance at very low concentration levels the said indicating layer must form a raised surface having a thickness of at least 5 microns but not more than 500 microns with the raised surface defining a coating formed by any conventional coating or printing process.

In one arrangement the said indicating layer is coated or printed in a shape of a predetermined warning symbol on the surface of a chemically inert substrate having color equal or similar to the color of the unreacted indicating layer.

In another arrangement, for the shape of the warning sign to appear in the presence of the targeted toxic substance, the said indicating layer is superimposed with a clear inert material impermeable to gases and vapors, having an opening in the shape of the said warning sign.

Still another arrangement for the warning sign to appear in the presence of the targeted toxic substance is to coat or print a transparent material impermeable to gases and vapors on the surface of the said screen in this way covering a part of the indicating layer which has the predetermined shape of the said warning symbol.

BRIEF DESCRIPTION OF THE DRAWINGS

The unique features and characteristics, which are considered for this invention, are set forth in particular in the appended claims. Additional objectives and advantages of the present invention will be best understood from the description of preferred embodiment when read in connection with the accompanying drawings of which:

DESCRIPTION OF THE PREFERRED EMBODIMENTS

The present invention generally relates to self-appearing warning signs and a method and arrangements for its manufacturing which warn the presence and measure the concentration of certain toxic gases and vapors in the surrounding environments. The self-appearing warning sign functions as a personal, calorimetric dosimeter or label for immediate, on-site, real-time warning for the presence and measurement of the concentration of targeted toxic gases and vapors. The self-appearing warning sign (1) of the present invention as illustrated in FIGS. 1 to 13, is a disposable, thin, light weight device preferably rectangular in shape, although any geometry would be acceptable, provided it may be easily worn near the breathing zone of a person without disturbing or affecting his or her job activities. The warning sign appears when a certain level of a particular contaminant in the atmosphere exceeds a preset, predetermined and pre-adjusted value. The average concentration of the targeted contaminant can be determined by measuring the color intensity of the self-appearing warning sign and relating it to the exposure dose over a certain period of time. The exposure dose is determined by visual matching with predetermined color scales or by electronic measurement as described in U.S. Pat. No. 5,468,645.

Figure 1:
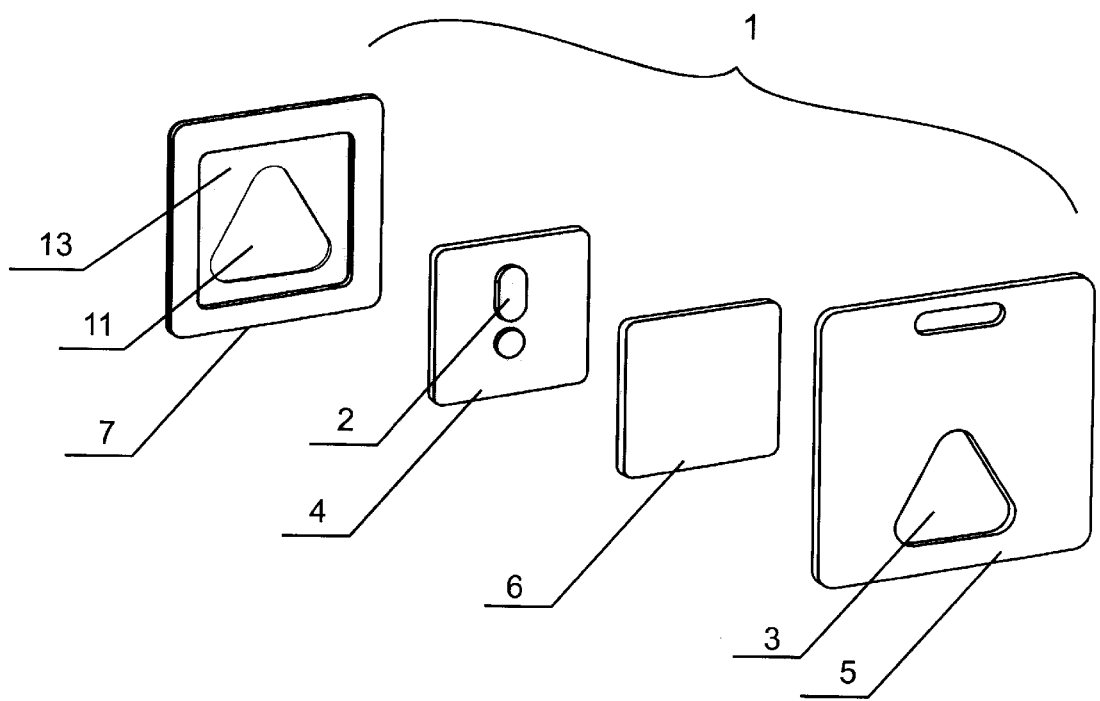
FIG. 1 is an isometric exploded view of one embodiment of the self-appearing warning sign wherein the said indicating layer is coated or printed in the shape of the said warning sign on an inert surface having similar color and appearance to the said indicating layer before exposure to the ambient atmosphere.

FIG. 1 is an exploded isometric view showing one embodiment of the warning device 1 of the present invention, wherein an indicating layer 2 is coated or printed over a plastic nonreacting support substrate 4 to a raised uniform thickness of between 5 and 500 microns. The thickness of the indicating layer 2 is an important characteristic of the indicating layer 2 affecting its sensitivity, color density and capacity as well as other metrological characteristics. If the thickness of the indicating layer 2 is not controlled to a thickness of at least 5 microns and preferably above 5 microns little advantage exists over using paper impregnated with an indicator in terms of its shelf life and humidity resistance. The indicating layer 2 is composed of a selected chemical formula which will change from one color to another in response to the presence of a particular toxic gas and/or vapor in the atmosphere. For example, lead acetate will change color in an irreversible manner from white to black in the presence of hydrogen sulfide and bromophenol blue will change color in a reversible manner from blue to yellow in the presence of hydrochloric acid.

The said indicating layer 2 may be deposited over the entire surface of the substrate 4 or may be deposited over the substrate 4 in a given shape or geometry to define a predetermined warning symbol or warning word. The color of the said substrate 4 is visually compatible with the color of the indicating layer 2 prior to the exposure of the device 1 to targeted hazard. The said support 4 is made by polycarbonate, polyethylene, polypropylene, polyvinyl or other inert material capable of being colored without affecting its chemical properties. A porous protective screen 6 permeable to the diffusion of light, gases and vapors separates the cover 5 from the coated indicator layer 2 and underlying support 4. The protective screen 6 is constructed from a porous hydrophobic inert clear plastic preferably of polypropylene, nylon or polyester, although any substance that has similar properties can be used. The mesh size of the porous protective screen 6 is predetermined depending on the properties of the chosen screen substance. The support 4 with the coated indicator layer 2 and protective screen 6 are enclosed by the cover 5 which is located at the front end of the device 1 and by another cover 7 located at the opposite or rear end of the device 1. The cover 7 is preferably of a picture frame construction having a relatively thin inner section 13 surrounded by an outer perimeter of thicker construction. As a result of this picture frame construction the inner section 13 forms a pocket in which the inert plastic support 4, coated indicating layer 2 and protective screen 6 may be placed so that upon assembly of the device 1 the front cover 5 can be securely held in abutment against the perimeter of the cover 7 to provide a sealed gas tight enclosure except for a cutout portion 11 in the rear cover 7 and a similar cutout portion 3 in the front cover 5. The cutout portion 11 is preferably of a triangular shape and the cutout portion 3 may likewise be of a triangular geometry although any desired geometry may be used.

Figure 2:
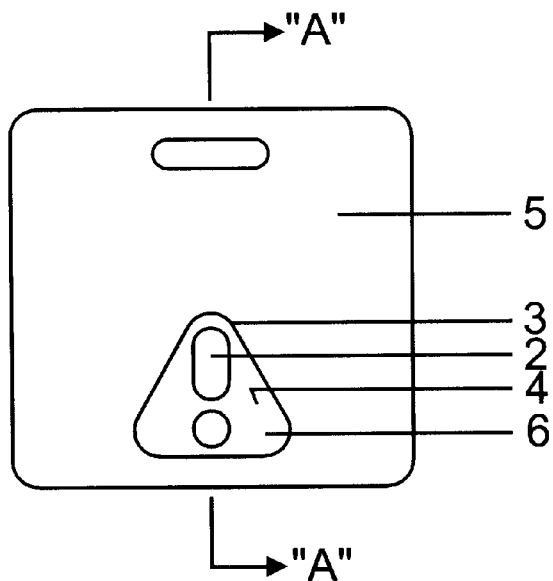
FIG. 2 is a top view of the self-appearing warning sign shown in FIG. 1.

In FIG. 1 the triangle 3 represents an opening in the front cover 5. The front cover 5 is constructed from any thin material of preferably plastic composition having good rigidity and which is chemically inert to the targeted substance to be detected. Accordingly, the preferred composition for cover 5 is polystyrene or polypropylene. The protective screen 6 should be permeable to the diffusion of light, gases and vapors and is accordingly, constructed from a hydrophobic inert clear plastic preferably of polypropylene, polyethylene or nylon or of any substance that has similar properties. Once exposed to a targeted substance such as a toxic gas the indicating layer changes color to provide a visible indication of a warning and since the indicating layer is of a predetermined geometry the warning immediately identifies the hazard. FIG. 2 is a top view of the embodiment shown in FIG. 1.

Figure 3:
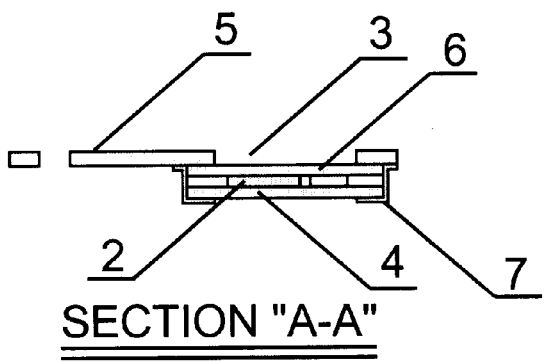
FIG. 3 is a cross sectional side elevation of the self-appearing warning sign shown in FIG. 1.

FIG. 3 is a cross sectional side elevation of the embodiment shown in FIG. 1.

Figure 4:
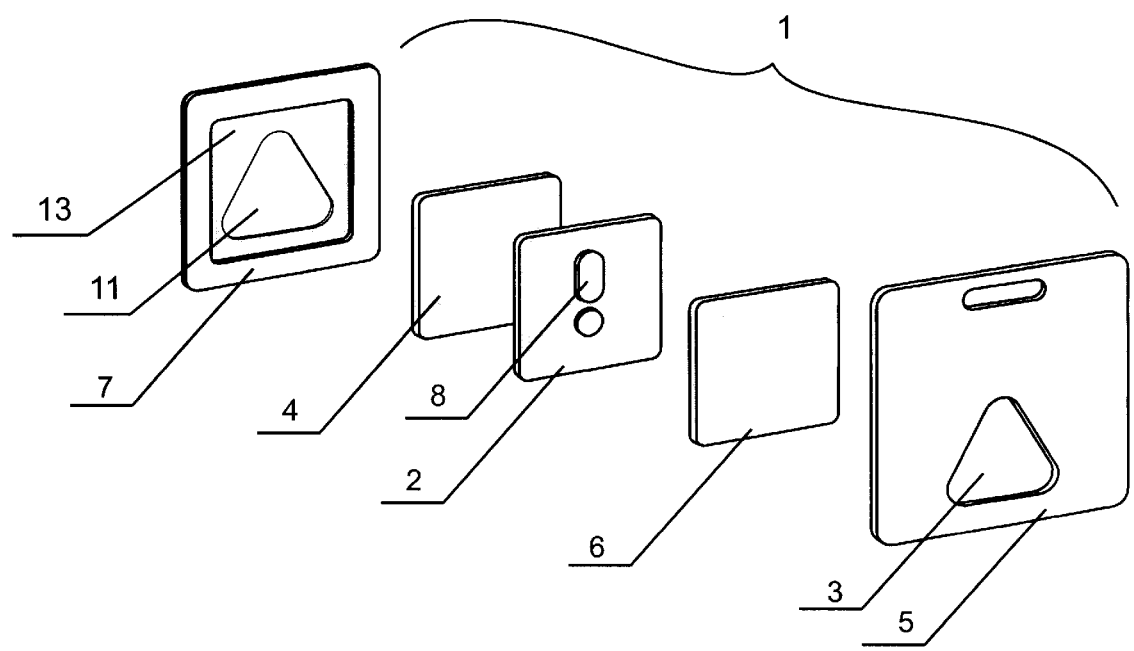
FIG. 4 is an isometric exploded view showing another embodiment of the selfappearing warning sign of the present invention in which an inert material impermeable to gases and vapors, having similar color and appearance to the said indicating layer, is printed or coated on top of the said indicating layer in the shape of the said warning sign.

FIG. 4 shows an isometric exploded view of another embodiment of the device 1 of the present invention wherein corresponding members of the device in each embodiment have been given the same reference numerals. The indicating layer 2 is coated over the entire surface of the inert plastic support 4 to the desired thickness between 5 and 500 microns. For this embodiment the inert plastic support 4 is preferably a clear plastic. A particular warning symbol such as an exclamation mark 8 is printed or coated on top of the indicating layer 2 using an inert material impermeable to gases and vapors and having the same color and appearance as the indicating layer 2 prior to exposure to the targeted substance to be detected. The impermeable material used in coating or printing the exclamation mark 8 is preferably silicon polycarbonate or polyester, however any substance having similar properties can be used. The protective screen 6 is placed between the cover 5 and the exclamation point 8 and covers the same surface area as does the indicating layer 2. The plastic support 4, the indicating layer 2, the -exclamation mark 8 and the protective screen 6 are all positioned in a manner to have the exclamation mark 8 in the center of the triangle opening 3 in the cover 5. Similar to the embodiment of FIG. 1 the outer cover 7 has an inner relatively thin section 13 which forms a pocket to secure the plastic support 4, the indicating layer 2, the exclamation mark 8 and the protective screen 6 for forming a sealed enclosure except for the triangular openings 3 and 11 when the device 1 is fully assembled.

Figure 5:
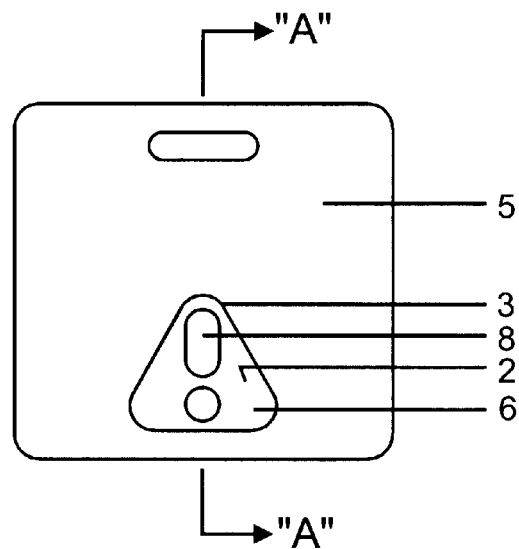
FIG. 5 is a top view of the self-appearing warning sign of FIG. 4.

FIG. 5 is a cross sectional side elevation of the embodiment shown in FIG. 4.

Figure 6:
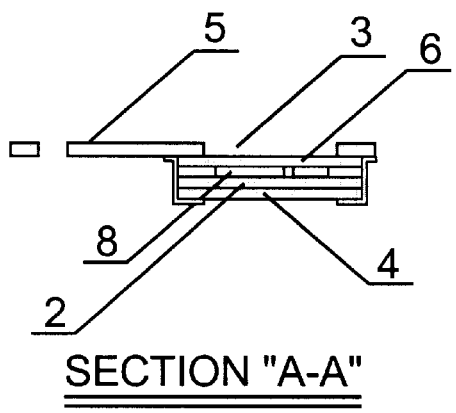
FIG. 6 is a cross sectional side elevation of FIG. 5.

FIG. 6 is a top view of the embodiment shown in FIGS. 4 and 5.

Figure 7:
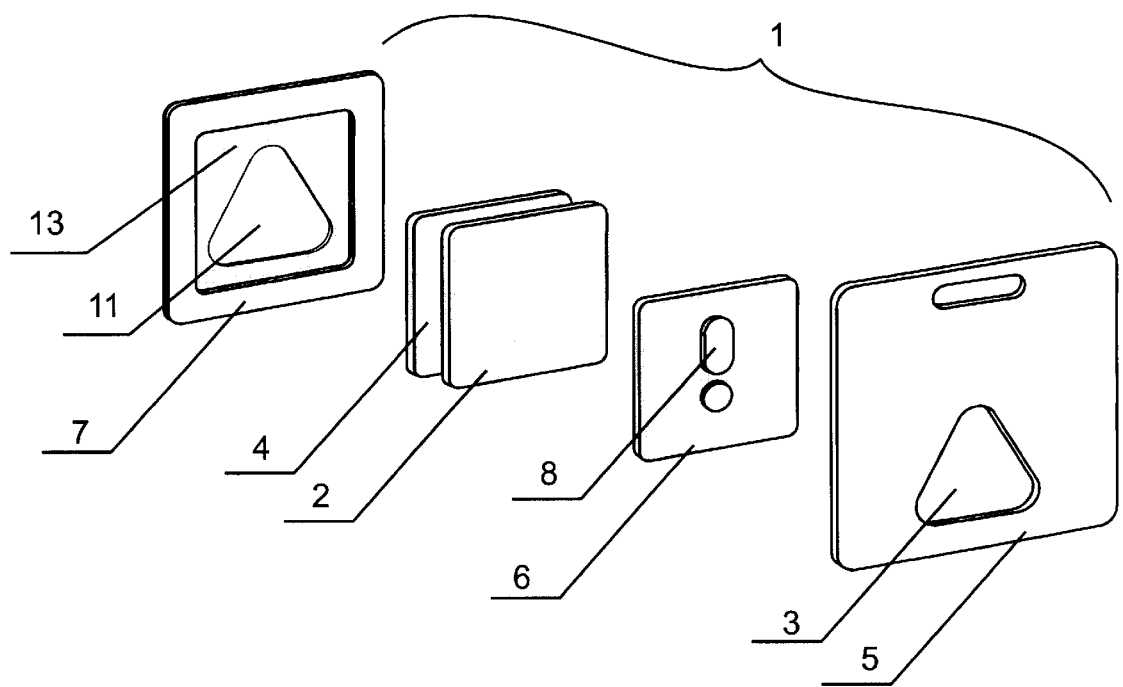
FIG. 7 is an isometric exploded view showing yet another embodiment of the self appearing warning sign wherein the said indicating layer is superimposed with a warning sign printed or coated on the protective screen.

FIG. 7 shows an isometric exploded view of yet another embodiment of the device 1 of the present invention wherein corresponding members of the device in each of the embodiments of FIGS. 1, 4 and 7 have been given the same reference numerals. In this embodiment the indicating layer 2 is coated over the surface of a clear chemically inert plastic support 4 and a desired symbol such as the exclamation mark 8 is printed or coated on the protective screen 6 instead of on the indicator layer 2 as in the embodiment of FIG. 4. Otherwise the operation of the embodiments 4 and 7 are substantially the same in that a warning sign representing a specific hazard defined by the geometry of the coated or printed exclamation mark 8 becomes visible against the background indicator 2 upon exposure to a hazardous gas. The exclamation mark 8, which is of an inert material impermeable to gases and vapors, acts as a mask to block the area of the indicating layer 2 underlying the exclamation mark 8 from changing color after exposure of the device to a targeted hazardous gas. The configuration of the exclamation mark defines a specific hazardous gaseous substance.

Figure 8:
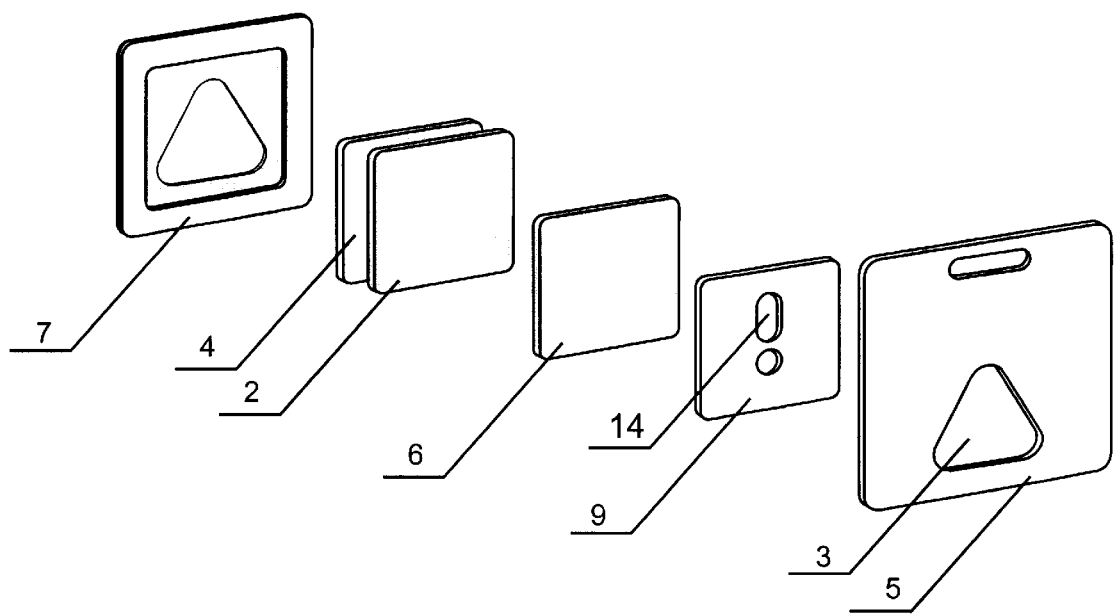
FIG. 8 is an isometric exploded view showing yet another embodiment of the selfappearing warning sign wherein the said indicating layer is superimposed with clear inert material having an opening in the shape of the warning sign.

FIG. 8 shows an exploded view of yet another embodiment of the device 1 of the present invention wherein corresponding members of the device in each of the embodiments of FIGS. 1, 4, and 7 have been given the same reference numerals. In this embodiment the indicator layer 2 is coated on a clear chemically inert plastic support surface 4 similar to FIG. 7 with the protective screen 6 superimposed on the indicator coating 2. In addition a transparent inert plastic 9 in the form of a sheet or coating is superimposed over the protective screen with the transparent inert plastic 9 having an opening 14 cutout in the shape of a desired symbol such as an exclamation mark to function in the same manner as in FIGS. 4 and 7 upon exposure of the device 1 to a targeted hazardous substance. The transparent inert plastic 9 is preferably constructed from polyester, polyethylene or polycarbonate, however any substance with similar properties can be used.

Figure 9:
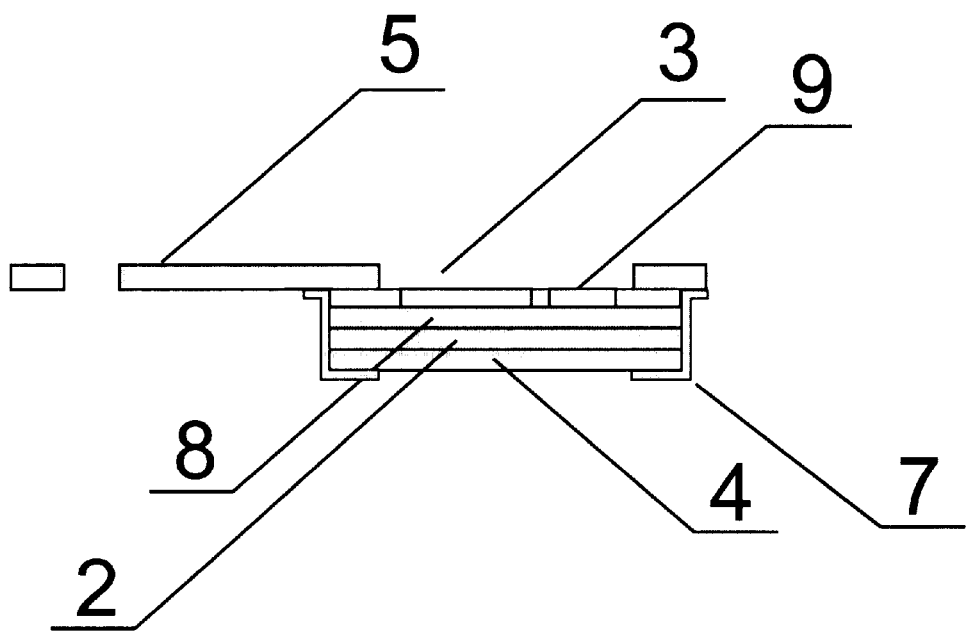
FIG. 9 is a cross sectional side elevation of the self-appearing warning sign shown in FIG. 8.

FIG. 9 is a cross sectional side elevation of the embodiment of FIG. 8.

Figure 10:
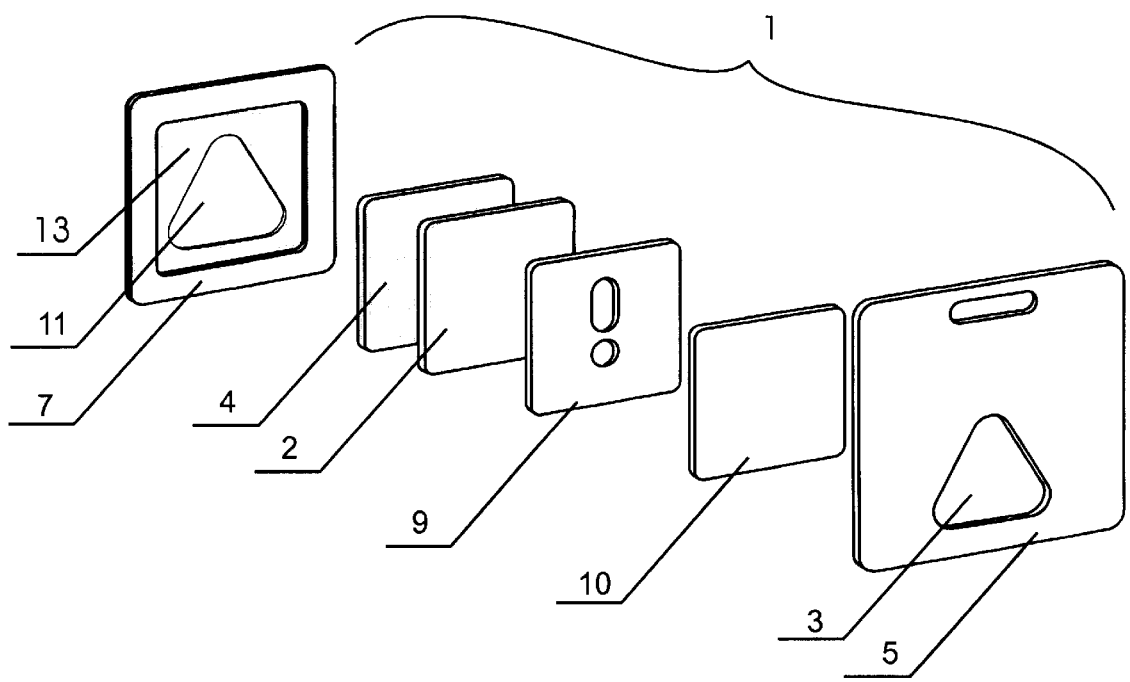
FIG. 10 is an isometric exploded view showing still another embodiment of the self-appearing warning sign wherein the warning sign appears on the other side.
Figure 11:
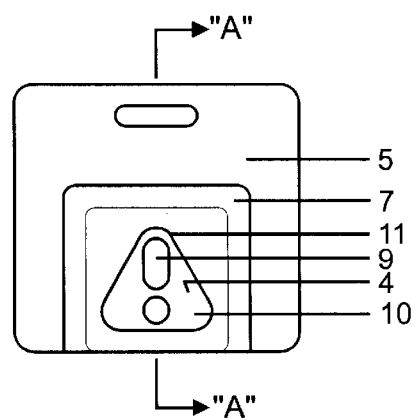
FIG. 11 is a back-view of the self-appearing warning sign shown in FIG. 10.
Figure 12:
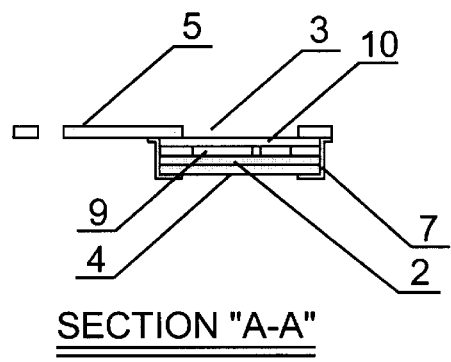
FIG. 12 is a cross sectional side elevation of the self-appearing warning sign shown in FIG. 11.
Figure 13:
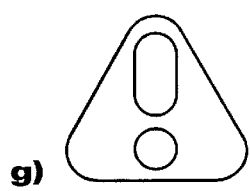
FIGS. 13a through 13j show other preferred warning signs to be used in the embodiment shown in FIGS. 1 through 12.
Figure 13:
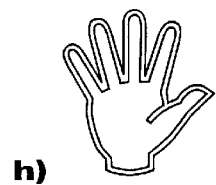
Figure 13:
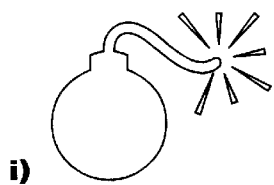
Figure 13:

FIG. 10 is an isometric exploded view of yet another embodiment of the present invention similar to embodiment 8 employing a transparent inert plastic material 9 with a cutout in a desired shape such as an exclamation point to provide a particular warning for a given hazard upon exposure of the device 1 to such hazard in the atmosphere. This embodiment also includes a diffusive resistance layer 10 preferably constructed from porous polyester, nylon or cellulose which is superimposed over the transparent inert plastic 9 so that an observer can view the formation of the warning sign appearing through the opening 11 in the rear of the embodiment Gases and vapors can diffuse only through the opening 3 but can be visually observed from the opening 11. FIG. 11 is a back-view of the self-appearing warning sign shown in FIG. 10 and FIG. 12 is a cross sectional side elevation of the self-appearing warning sign shown in FIG. 11.

In all of the embodiments shown in FIGS. 1 through 12 the said exclamation point is used as a simple example and could be replaced by other symbols or words as shown in FIGS. 13a through 13j for conveying a warning of a particular danger corresponding to the spirit of the invention. It is in the spirit of this invention that the self-appearing warning sign could be a combination of words and symbols or self-appearing words or symbols in combination with preprinted words, symbols, or text.

What we claim is:

1. A method for forming a portable detection device which constitutes a self-appearing warning sign responsive to the presence of a specified polluting or hazardous gas in the ambient atmosphere comprising the steps of: depositing a coating composition containing one or more chromophoric reagents which will cause a visible color change in the presence of said specified polluting or hazardous gas upon a thin gas impermeable support member which is transparent or of a color visually equivalent to the color of the unreacted coating composition with said coating composition being deposited to form an indicating layer having a raised thickness of between about 5–500 microns, placing a transparent porous screen hydrophobic member which is inert to the atmosphere over said indicating layer with said indicating layer being visible through said porous screen, masking a designated area of said indicating layer using a material composition impermeable to gaseous vapors to form a designated pattern which provides a warning sign identifying the presence of said polluting or hazardous gas upon exposure of said device to the atmosphere, and assembling said coated support member and said transparent porous screen hydrophobic member between plastic covers arranged on opposite ends of said device to form an enclosure with each cover having an opening therein for exposing the device to the atmosphere and with said porous screen hydrophobic member being impervious to the atmosphere and having a mesh size so as to readily permeate gases and vapor and to maintain a sufficient separation between said indicating layer and said cover for protecting the indicating layer from the atmosphere and to permit direct visual access of the color change in the coating defining the warning signal by an outside observer after said device is exposed to said polluting gas directly through the opening located on the porous screen side of the device facing the indicating layer and that a color change is also visible by looking through the opening in the cover exposed to the atmosphere on the opposite side of the device.

2. A method as defined in claim 1 wherein said warning sign has a predetermined shape selected from the group consisting of: an exclamation point, a known symbol for a poison or danger, or one or more letters or words representing a hazardous condition selected from the group consisting of: DANGER, POISON, WARNING, HAZARD, HF and $H_2S$.

3. A method as defined in claim 2 wherein said coating composition forming said indicating layer is deposited by a coating or printing process.

4. A method as defined in claim 3 wherein said masked designated area is formed directly on the indicating layer.

5. A method as defined in claim 3 wherein said masked designated area is formed on the hydrophobic member.

6. A method as defined in claim 3 wherein said masked designated area is formed on a separate plastic sheet containing a cutout portion in a desired pattern.

7. A method as defined in claim 6 wherein said separate plastic sheet lies adjacent to said hydrophobic member and to a cover at one end of said device.

8. A portable self-appearing warning sign for detecting the presence of a specified polluting gas in the ambient atmosphere comprising a thin gas impermeable support member which is visually transparent, a coating superimposed upon said support member having a composition containing one or more chromophoric reagents which will cause a visible color change in the presence of a specified polluting gas with said coating having a raised thickness of between about 5–500 microns and with said coating being formed in a given geometry corresponding to a warning of said polluting gas at a predetermined minimum concentration level, a transparent porous screen hydrophobic member inert to the atmosphere located over said coating with said coating being visible through said porous screen and with said coating and said porous screen being arranged between opposite plastic covers impervious to the atmosphere to form an enclosure with each cover having an opening to the atmosphere of a predetermined geometry, said porous screen member having a mesh size sufficient to permeate gases and vapors and to maintain a sufficient separation between said coating and said cover for protecting the coating from the atmosphere while permitting direct visual access to the warning sign formed by the coating through the opening on the porous screen side of the device facing the coating and that a color change is also visible by looking through the opening in the cover exposed to the atmosphere on the opposite side of the device.

9. A portable self-appearing warning sign as defined in claim 8 with the opening in each cover being in relative alignment to one another on opposite ends of said device.

10. A portable self-appearing warning sign as defined in claim 9 wherein one of said covers is a laminated structure having a thick outer perimeter surrounding a thin layer so as to form a pocket for housing said support member and hydrophobic member in a gas tight relationship with the other cover.

* * * * *